United States Patent [19]
Kay

[11] Patent Number: 5,662,683
[45] Date of Patent: Sep. 2, 1997

[54] OPEN HELICAL ORGANIC TISSUE ANCHOR AND METHOD OF FACILITATING HEALING

[75] Inventor: David B. Kay, Akron, Ohio

[73] Assignee: Ortho Helix Limited, Barberton, Ohio

[21] Appl. No.: 517,259

[22] Filed: Aug. 22, 1995

[51] Int. Cl.⁶ .................................................. A61B 17/00
[52] U.S. Cl. .................... 606/232; 606/73; 606/151; 411/425
[58] Field of Search ................. 606/232, 75, 73, 606/72, 65, 60, 151; 623/13; 411/392, 425; 24/711.2, 711.3

[56] References Cited

U.S. PATENT DOCUMENTS

| | | |
|---|---|---|
| 2,414,882 | 1/1947 | Longfellow ........................ 606/73 |
| 2,570,465 | 10/1951 | Lundholm ........................ 606/73 |
| 3,499,222 | 3/1970 | Linkow et al. . | 
| 4,590,928 | 5/1986 | Hunt et al. . |
| 4,870,957 | 10/1989 | Goble et al. . |
| 5,053,047 | 10/1991 | Yoon ........................ 606/232 |
| 5,203,787 | 4/1993 | Noblitt et al. . |
| 5,268,001 | 12/1993 | Nicholson et al. . |
| 5,370,662 | 12/1994 | Stone et al. ........................ 606/232 |
| 5,417,691 | 5/1995 | Hayhurst . |
| 5,582,616 | 12/1996 | Bolduc et al. ........................ 606/143 |

FOREIGN PATENT DOCUMENTS

| | | | |
|---|---|---|---|
| 374088 | 6/1990 | European Pat. Off. | 606/73 |
| 0663184 | 7/1995 | European Pat. Off. | 606/232 |
| 1071297 | 2/1984 | U.S.S.R. | 606/65 |
| WO94/28811 | 12/1994 | WIPO | 606/73 |

*Primary Examiner*—Jeffrey A. Schmidt
*Attorney, Agent, or Firm*—Hudak & Shunk Co., LPA

[57] ABSTRACT

The invention relates to a tissue anchor which is an open helix of biocompatible material having a slope of from 0.5 to 10 turns per centimeter, a length from 3 to 75 millimeters, a diameter of from 1.5 to 11 millimeters, and an aspect ratio of from about 3 to about 5 to 1. The anchor can have a head which is capable of securing or clamping tissue together, such as holding a suture to secure a ligament or tendon to bone. The anchor can also have a head which causes an inward, compressive loading for use in fastening bone to bone, orthopedic plates to bone, or cartilage to bone.

16 Claims, 3 Drawing Sheets

OPEN HELICAL ORGANIC TISSUE ANCHOR AND METHOD OF FACILITATING HEALING

FIELD OF INVENTION

The present invention relates to tissue anchors as well as to methods of promoting healing or repairing hard or soft, living, organic tissue using an open helix anchor.

BACKGROUND OF THE INVENTION

The present invention relates to an anchor (or connector) which can be used to fasten organic tissue in close proximity in order to afford the tissue the opportunity to heal. The anchor of the present invention can be used to anchor and clamp dense, regular and/or dense, irregular connective tissue in place in relation to bone. The anchor can also be used for cartilage transplants, i.e., for holding cartilage in fixed relation to bone, and can also be used in bone as a buttress, such as for buttress plating techniques, or to fasten pieces of bone together as a screw substitute.

As compared to the prior art, the anchor of the present invention allows a method of holding together organic tissue with minimal disruption to the biological environment or to the tissue itself. For example, prior art devices and methods customarily require a large hole for insertion of the anchoring device, causing not only structural damage to the implantation site, but also inflicting further trauma to the biological site such as generating heat, introducing further possibility for infection, and destroying bone which may be needed to help heal the repaired area. Such trauma is amplified in cases where prior art devices malfunction during the implant procedure. Hooks or screws can get stuck and further obscure the operating site or require tedious removal.

The anchor of the present invention may be very useful for applications such as anchoring ligaments or tendons when performing soft tissue surgical reconstruction, ruptured tendons, or torn ligaments, in which the surgeon wants to reconstruct or repair connective tissue with respect to the bone.

The anchoring device functions to hold together the tissue (such as connective tissue to bone) for a relatively limited time frame, e.g., six to twenty-six weeks, during which time the biological system will heal.

The anchor of the present invention can be used with advantage in many of the same applications in which cancellous screws are used in addition to applications in which traditional prior art anchoring techniques are unsatisfactory. The anchor of the present invention is far less invasive to implant than cancellous screws or hook-style anchors, i.e., the implant has a minimized mass, the insertion point is small relative to the size of the implant, and the device involves minimal removal of native tissue. In addition, the area of bone which is needed to secure the present invention can be of poorer quality than for prior art devices.

Additionally, the anchor of the present invention can be removed and minimally reangulated in order to utilize the same surgical site. Prior art devices require a large hole (relative to implant size) to be drilled in order to implant the device, and once the hole is contaminated by malfunction or misalignment of the device, it is necessary to drill another hole far enough away to achieve stability in a new location. Given the surgical context, this is extremely inconvenient.

The anchor of the present invention can be used in methods of ligament, tendon, or other tissue repair. For example, the anchor can be used for a method involving cartilage transplant and it can be used alone or in conjunction with a plate for a method of buttressing bone where the quality of bone may be questionable due to trauma or degenerative disease. The anchor may be used in methods of fixation involving connective tissue repair and replacement and may be inserted using a plunge-handle or "T" handle inserter which utilizes longitudinal travel in order to achieve rotational insertion.

Specifically, the anchor is used in ligament or tendon repair in which a pilot hole, having a diameter much smaller than the outer diameter of the helical anchor, is drilled in the cortex of the bone. The angle of implantation can be varied as necessary. The anchor is subsequently mounted or loaded into the insertion tool, threaded into the pilot hole, and screwed into the bone an appropriate distance so that the anchor head can be accessed but is not obtrusive. The ligament or tendon is attached to the anchor, such as by suturing.

SUMMARY OF THE INVENTION

The anchor in accordance with the invention comprises an open helical structure which is a constant or varied-diameter, elongate member, fiber, or filament comprised of a relatively rigid, biocompatible material such as a wire having a diameter which may vary optimally from about 0.2 millimeters to about 5.0 millimeters. The length of the anchor will depend upon the particular application, but will range generally from about 3.0 millimeters to about 75.0 millimeters with the upper ranges being useful for buttressing techniques. The outer diameter of the helix will also vary in accordance with the application, but it will range generally from about 1.5 millimeters to about 15.0 millimeters. A suitable rate of slope for the helix is from about 0.5 to about 10 turns per centimeter. The aspect ratio of the helix, which as used herein means the ratio of the helix outer diameter to the fiber diameter, is an important ratio in order to achieve the proper stiffness to enable insertion and to firmly seat in the bone; a suitable range is 3.5 to 4.5.

Advantageously, the anchor of the present invention involves relatively simple, cost-effective manufacturing processes. The present anchor is also less intimidating to doctors and patients than prior art devices and can be used with simple, straight-forward instrumentation. Finally, since the device is relatively noninvasive, several can advantageously be used together in instances where more than one prior art device could not be used. It is preferred, but not necessary, that the helix has a constant circular diameter and a constant slope (meaning the rate of turn per unit of longitudinal length).

For its connective applications, the anchor includes an attachment head at one end which is suitable for securing the tissue or suture which is to be held. For example, in the case of a filamentary anchor, the anchor may have a hook, crossbar or eyelet. For applications in which the anchor secures rigid material such as cartilage or a buttressing plate, the head may have a surface which is designed to distribute the load evenly over the rigid material.

In a second embodiment, the anchor will have a modular head. For example, the helical anchoring portion may terminate at the superficial end in a post that will accommodate one of several head options. These head options may include a button, clamp, clip, snap, or rivet. At the other end, the anchor includes a cutting or self-tapping point.

In accordance with another embodiment of the invention, a buttressing system is provided which comprises a plate having at least two through bores which are each engaged by an open-helix anchor.

In accordance with a method of the present invention, an anchoring site is surgically accessed, the helical anchor is screwed into the anchoring site, and connective tissue is secured to the attachment head of the anchor.

In accordance with another method of the invention, a bone is buttressed by surgically accessing an implant site, aligning a plate having at least one aperture over the site, and securing the plate to the implant site by inserting an open-helix anchor through the aperture and into the implant site to anchor the plate with respect to the implant site.

DESCRIPTION OF TE DRAWINGS

DETAILED DESCRIPTION OF THE INVENTION

Figure 2:
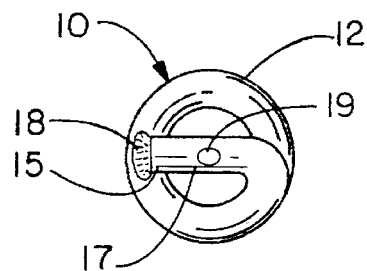
FIG. 2 is a top view taken of FIG. 1.
Figure 1:
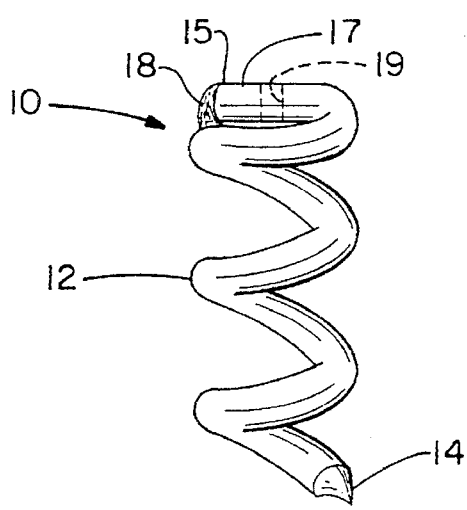
FIG. 1 is an elevational view of the anchor device showing the attachment head in side elevation.
Figure 3:
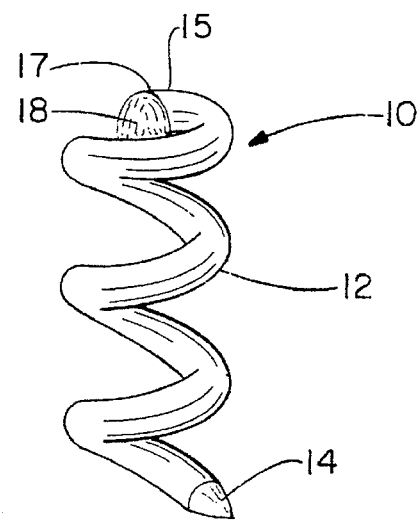
FIG. 3 is an elevational view, similar to FIG. 1, but showing the anchor rotated 90° to the right so that the attachment head is seen in an end view.

In accordance with the invention, FIGS. 1–3 illustrates the anchoring device in accordance with the invention enlarged to show the invention in detail generally at 10. The anchoring device 10 comprises an open helix 12 having a pointed insertion tip 14 at one end and an attachment head 15 at the other end.

Preferably, the anchoring device is comprised of a rigid, biocompatible material having a high-yield strength such as stainless steel or titanium. The device can also be made from a biodegradable material such as polyglycolic acid ("PGA"), polylactic acid ("PLA"), polydiaxone hydroxy apatite ("PDA"), and the like. For example, the device 10 may be made from surgical-grade titanium or stainless steel wire having a wire diameter ranging from about 0.4 millimeters to about 3.0 millimeters, and more specifically from about 0.5 millimeters to about 2.0 millimeters, and most specifically from about 1.0 millimeters to about 2.0 millimeters. Optionally, the helix diameter may be of variable cross-section ranging from a smaller-diameter wire at the insertion tip to a larger-diameter wire near the attachment head 15.

The "slope" of the helix is used herein to mean the number of turns (i.e., one 360° rotation) per unit length and varies from about 0.5 turn per centimeter to about 10 turns per centimeter, and more specifically from about 0.5 turn to about 4 turns per centimeter, and most specifically from about 1 to about 2 turns per centimeter. The anchor generally comprises a length of helix sufficient to achieve from 0.75 to 4 complete 360° revolutions, or more specifically from about 1 to about 3 revolutions. Accordingly the length of the anchor for most general fastening or anchoring applications is from about 3 to about 18 millimeters, and more specifically from about 4 to about 15 millimeters, and most specifically from about 8 to about 15 millimeters. For plating or buttressing applications, the length of the anchor will generally range from about 5 to about 75 millimeters, preferably from about 5 to about 40 millimeters and most preferably from about 10 to about 20 millimeters.

The overall outer diameter of the open helix portion 12 of the anchoring device 10 ranges from about 1.5 to about 11 millimeters, and more specifically from about 3 to about 9 millimeters, and most specifically from about 5 to about 7 millimeters. The wire is generally circular in cross-section, although it is envisioned that it may be angular such as diamond-shaped or rhombohedral.

It is important that the anchor have an aspect ratio of from about 3 to about 5, preferably from 3.5 to 4.5, and most preferably around 4. As used herein, aspect ratio means the ratio of the helix outer diameter to the wire diameter. If the ratio is too large, the device is too rigid, whereas if the ratio is too small, the device is overly flexible.

The attachment head 15 of the anchoring device 10 may vary according to the specific application. For example, it may be desirable to include a broader compression area for direct attachment of connective or soft tissue to bone, as compared to suture techniques involving suturing or wiring the soft tissue in place with respect to the anchoring device. Examples of attachment heads suitable for suturing or wiring connective tissue include crossbars, hooks and eyelets.

FIG. 1 illustrates an attachment head 15 having a crossbar 17 which arches slightly above the last helical turn and is attached such as by spot welding 18 at the terminal end. It may be further preferable to include an opening 19 or cannulation in the crossbar to allow for cannulated surgical techniques (i.e., placement of the anchor over a positioned wire 60 which may be subsequently removed). The opening may range in size from 0.5 millimeters to 1.5 millimeters depending on the application.

Figure 4:
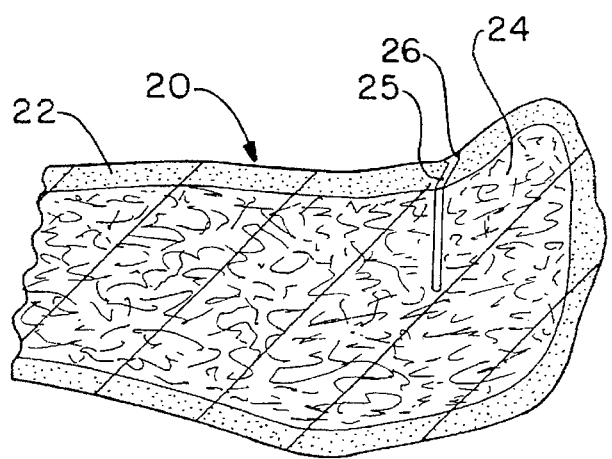
FIG. 4 illustrates the pilot hole in the bone prior to insertion of the anchor.
Figure 5:
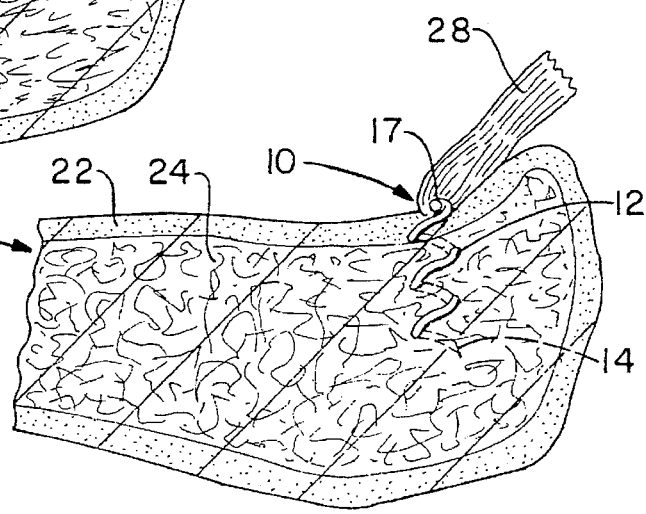
FIG. 5 illustrates an anchor in place in the cancellous portion of the bone with the attachment head projecting above the surface of the bone in order to allow attachment of the soft tissue to the anchor.

The device and method of the invention are illustrated in FIGS. 3–5. In particular, FIG. 4 illustrates a section of bone generally at 20 having a cortex 22 and a cancellous portion 24. A pilot hole 25 has been drilled in the cortex 22 in order to ease insertion of the anchoring device 10. A countersink hole 26 through the cortex is also illustrated.

FIG. 5 illustrates the anchoring device 10 as it has been partially implanted through the pilot hole 25 into the cancellous portion of the bone. In some instances where the cortex is particularly thin, a pilot hole may be unnecessary. The soft tissue is attached to the anchoring device when the device is in position such as by suturing or wiring to the attachment head 15 of the anchoring device 10.

Figure 6:
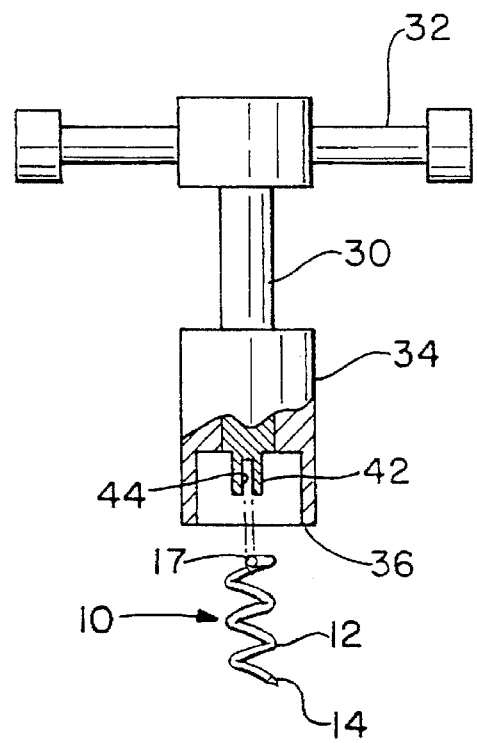
FIGS. 6 and 7 illustrate the tool which may be used for inserting the anchor.
Figure 7:
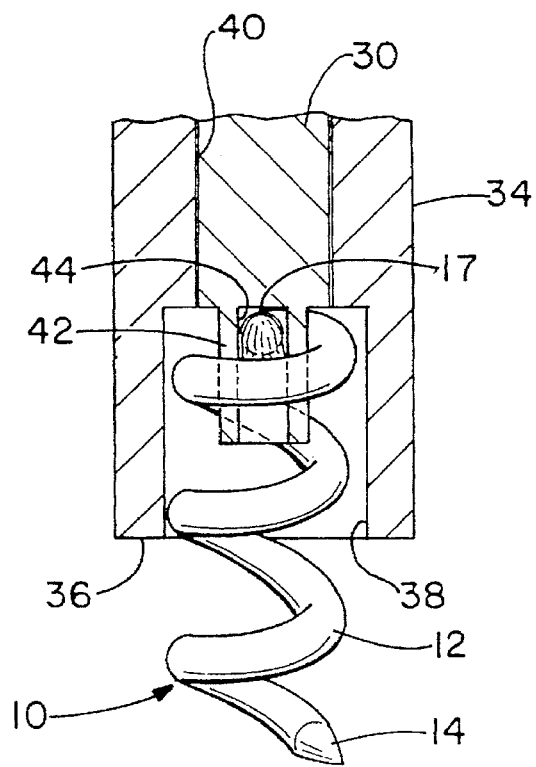
Figure 8:
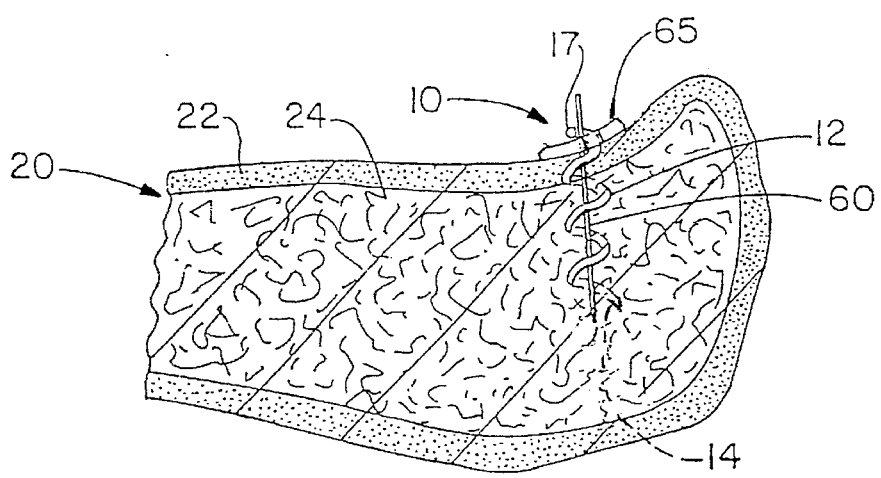

FIGS. 6 and 7 illustrate an instrument which can be used for the implantation of the anchor in accordance with the present invention. Specifically, the instrument includes a central shaft 30 having a T-shaped handle 32 designed to allow the surgeon to easily grasp the handle 32 and rotate the shaft 30 to screw the anchor 10 into the bone through the optional pilot hole. The placement guide 34 includes a bottom surface 36 which can rest against the cortical surface where the anchor 10 is to be implanted. The guide 34 further includes an internal opening 38 having a diameter sufficient to receive the top portion of the anchor 10. The guide 34 further includes a bore 40 which provides a bearing surface for the shaft 30. At its lower end, the shaft 30 includes a head 42 having an internal slot 44 which receives the crossbar of the anchor 10 to enable the surgeon to apply torque to the anchor. The head 42 has an external diameter which cooperates with the internal diameter of the anchor 10. Optionally, the shaft 30 may also include a longitudinal, internal opening to receive a guide wire 60 to allow for further cannulated surgical techniques. The anchor 10 may also be used in conjunction with a plate 65.

During use of the anchor of the present invention, the attachment location is approached with standard surgical exposure. A pilot hole is drilled through the near cortex only and a drill sleeve is used to protect surrounding soft tissues. The anchoring device 10 is inserted with an insertion tool such that the attachment head 15 is left out of the bone. The angle of insertion may be perpendicular to the bone surface or at a 45° angle. A suture may be passed under the exposed crossbar 17 of the attachment head 15 once or twice, depending on the surgeon's choice. The attachment tool is then used to countersink the attachment head 15 below bone level. The ligament or tendon is then sutured into place with a preferred suturing method such as Bunnell, whip, or modified Kessler. The wound is subsequently closed and the procedure is completed in standard fashion.

EXAMPLE

Six samples of surgical-grade, stainless steel bone anchors in accordance with the invention were placed in a sample of artificial cancellous bone. Two samples each had a total longitudinal length of about 20 millimeters. The other four samples each had total lengths of about 13 millimeters. The outer diameter of all samples was 5 millimeters and the wire diameter was 1.5 millimeters. Both long samples and two short samples had attachment heads which were crossbars and were attached by heliarc spot welding. The other short samples had crossbar attachment heads which were not welded.

Pullout tests were conducted using an MTS instrument. Straight, longitudinal pull was applied to the embedded anchors; this reproduced the least favorable condition for pullout characteristics. The results are shown in the table below. "Displacement" refers to bending of the crossbar in the longitudinal direction.

TABLE I

| PLASTIC DEFORMATION | | |
| --- | --- | --- |
| SHORT/NON-WELDED | SHORT/WELDED | LONG/WELDED |
| Average 48 lbs. with 2 millimeters of displacement | Average 52 lbs. with 2.2 millimeters of displacement | Average 58 lbs. with 2.4 millimeters of displacement |

All of the numbers represent desirable anchoring values.

While in accordance with the patent statutes the best mode and preferred embodiment has been set forth, the scope of the invention is not limited thereto, but rather by the scope of the attached claims.

What is claimed is:

1. An organic tissue anchor comprising a rigid, biocompatible, elongate member having a diameter of from about 0.4 millimeters to about 3 millimeters comprising surgical-grade titanium or stainless steel wire or a bioabsorbable material which forms an open, helical structure having a length from about 3 millimeters to about 75 millimeters, an outer diameter of a constant dimension of from about 1.5 millimeters to about 15 millimeters, a slope from about 0.5 to about 10 turns per centimeter and having at a first end an insertion tip and at a second end an attachment head which is capable of connecting organic tissue to said anchor and which comprises a crossbar having an eyelet for receiving a suture.

2. An anchor according to claim 1, wherein the anchor is from about 2 to about 20 millimeters in length.

3. An anchor according to claim 2, wherein the elongate member has a diameter of from about 0.5 to about 2 millimeters and a length of from about 4 to about 18 millimeters.

4. An anchor according to claim 3, wherein the elongate member has a diameter of from about 1 to about 2 millimeters and a length of from about 8 to about 15 millimeters.

5. An anchor according to claim 3, wherein the helix achieves from about 0.5 to about 20 complete 360° revolutions.

6. An anchor according to claim 5, wherein the anchor achieves from about 1 to about 4 revolutions.

7. An anchor according to claim 2, wherein the overall outer diameter of the helix is from about 1.5 to about 11 millimeters.

8. An anchor according to claim 1, wherein the attachment head is cannulated.

9. A method of securing tissue comprising:
    accessing a surgical site including a tissue anchoring site in bone;
    implanting an anchor comprising an open, rigid, biocompatible helix into said site, said helix being formed from an elongate member having a circular cross-section with a diameter of from about 0.2 to about 5 millimeters, and said helix having a length of from about 2 to about 75 millimeters, a slope from about 5 to about 10 turns per centimeter, and an outer diameter of from about 1.5 to about 11 millimeters; and
    attaching a tissue to said anchor.

10. A method according to claim 9, wherein said step of attaching comprises suturing said tissue to said anchor.

11. A method according to claim 9, including a step of making a pilot hole which is about the diameter of the elongate member in the bone prior to the insertion to the anchor in the bone.

12. A method according to claim 11, wherein said attaching step comprises suturing a ligament or tendon to said anchor.

13. A method of buttressing bone comprising the steps of:
    accessing a surgical site including at least a first cortical bone surface aligning a plate having an aperture on said first cortical surface; and
    implanting at least one anchor through said plate aperture into at least said first conical surface, said anchor comprising an open helix having a length of from about 5 to about 75 millimeters, a slope of from about 0.5 to about 10 turns per centimeter, and said helix being formed from an elongate member having a circular cross-section having a diameter of from about 0.2 to about 5 millimeters, said helix having a constant outer diameter said helix further having at a first end an insertion tip and at a second end a head capable of applying a compressive force in the direction of the first end.

14. A bone anchor comprising a rigid, biocompatible, elongate member comprising a wire having a regular, solid cross-section with a diameter of from about 1.0 millimeter to about 2 millimeters which forms an open, helical structure having a length from about 3 millimeters to about 75 millimeters, an outer diameter of a constant dimension of from about 3 millimeters to about 9 millimeters, a slope from about 0.5 to about 4 turns per centimeter, and an aspect ratio of about 3 to about 5, said anchor having at a first end a bone insertion tip, and at a second end an attachment head having means for connecting organic tissue to said anchor, said attachment head being one piece with said helical structure, and said head having substantially the same outer diameter as said helix.

15. A bone anchor as set forth in claim 14, wherein said attachment head is welded directly to said helical structure.

16. A method of buttressing bone comprising the steps of:

accessing a surgical site including at least a first cortical bone surface;

implanting at least one anchor into at least said first cortical surface, said anchor comprising an open helix having a length of from about 5 to about 75 millimeters, a slope of from about 0.5 to 10 turns per centimeter, and said helix being formed from an elongate member having a circular cross-section having a diameter of from about 0.2 to about 5 millimeters, said helix having a constant outer diameter, said helix further having at a first end an insertion tip and at a second end a head capable of applying a compressive force in the direction of the first end and wherein said head is cannulated, and further including the steps of using a guide wire to achieve initial bone alignment and subsequently implanting said anchor about said guide wire by means of said cannulation.

* * * * *